United States Patent [19]

Zaiger et al.

[11] Patent Number: Plant 6,410

[45] Date of Patent: Nov. 22, 1988

[54] PEACH TREE ("DOUBLE JEWEL")

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 5,265

[22] Filed: Jan. 20, 1987

[51] Int. Cl.[4] ..... A01H 5/00

[52] U.S. Cl. ..... Plt./43

[58] Field of Search ..... Plt./43

*Primary Examiner*—James R. Feyrer

[57] ABSTRACT

A new and distinct variety of peach tree which is of large size, vigorous upright growth and bearing large size, attractive, double pink flowers in the spring, giving the appearance of a flowering type ornamental tree but being a productive and regular bearer of large size, yellow flesh, freestone fruit with good eating quality; the fruit is further characterized by having firm flesh, a yellow ground color which is overspread with an attractive red skin color.

1 Drawing Sheet

ORIGIN OF THE VARIETY

The present variety of peach tree was developed in the experimental orchard located at Modesto, Calif., from a cross between a selected nectarine seedling, which originated from an open pollinated Red Grand Nectarine (U.S. Plant Pat. No. 1,060) and a genetic dwarf peach of unknown parentage which produced attractive double pink flowers and large yellow flesh peaches. We grew and maintained these seedlings under close observation and we recognized its desirable dual purpose flowering and fruiting characteristics described above and selected the variety for reproduction.

ASEXUAL REPRODUCTION OF THE VARIETY

Asexual propagation of the new and distinct variety of peach tree by budding was performed in the experimental orchard at Modesto, Calif. and shows that said characteristics come true to form and are established and transmitted through succeeding propagations.

SUMMARY OF THE VARIETY

The present variety relates to a new and distinct variety of peach tree which is of large size, upright growth and bearing large, attractive, double pink flowers in the spring and is a regular and productive bearer of large, yellow flesh, freestone fruit ripening in late June at Modesto, Calif. The new variety is further characterized by having a high degree of attractive red skin color, uniform ripening and firm flesh with good eating quality.

BRIEF DESCRIPTION OF THE PHOTOGRAPHS

The accompanying color photographs show typical specimens of the foliage and fruit of the new variety, with the upper and lower surface of the leaves being illustrated and fruit specimens showing the exterior and a sectional view being depicted with a stone remaining in place. The illustrations were taken shortly after being picked at maturity (firm ripe) and the colors are as nearly true as reasonably possible in a color representation of this type.

DESCRIPTION OF THE VARIETY

A botanical detailed description of the new distinct variety of peach tree, its fruit, flowers and foliage, as based on observations of specimens grown at Modesto, Calif., with color terminology (except those in common color terms) are in accordance with Reinhold Color Atlas by A. Kornerup and J. H. Wanscher.

Tree:
- *Size.*—Large.
- *Vigor.*—Vigorous.
- *Form.*—Upright.
- *Production.*—Productive.
- *Density.*—Medium.
- *Bearing.*—Regular bearer.

Trunk:
- *Size.*—Large.
- *Texture.*—Shaggy.

Branches:
- *Size.*—Stocky to medium.
- *Texture.*—Medium rough.
- *Color.*—Grayish brown to reddish brown.

Leaves:
- *Size.*—Medium. Average length — 5½". Average width — 1⅜".
- *Texture.*—Smooth.
- *Margin.*—Crenate.
- *Petiole.*—Medium length. Medium thickness.
- *Glands.*—Primarily reniform — some leaves show both reniform and globose. Medium size. Numbers vary 1 to 4. Average number 2. Positioned on base of blade and upper portion of petiole.
- *Color.*—Upper surface — dark green (28-F-6) to (28-F-7). Lower surface — grayish green (28-E-5) to (28-E-7).

Flower buds:
- *Size.*—Large.
- *Form.*—Plump.
- *Pubescence.*—Pubescent.

Flowers:
- *Size.*—Large, showy, characterized as double flowers due to having two sets or more of petals on each flower.
- *Blooming period.*—Mar. 1, 1984 to Mar. 10, 1984. Varies slightly with climatic conditions.
- *Pollen.*—Present.
- *Color.*—Pink, showy.

Fruit:
- *Maturity when described.*—Firm ripe.
- *Date of first picking.*—June 20, 1984.

*Date of last picking.*—June 27, 1984.

*Size.*—Large. Average diameter axially $2\frac{1}{2}''$ to $2\frac{7}{8}''$. Average transversely in suture plane $2\frac{1}{2}''$ to $2\frac{7}{8}''$.

*Form.*—Globose to slightly flattened at stem end.

*Suture.*—Shallow, extends from base to apex, some fruit checked with small indentations.

*Ventral surface.*—Rounded, some fruit slightly lipped.

*Base.*—Retuse.

*Cavity.*—Rounded, some fruit slightly elongated in suture plane. Average depth — $\frac{1}{2}''$. Average breadth — $\frac{3}{4}''$.

*Apex.*—Rounded. Varies from slight point to small depression.

Skin:

*Thickness.*—Medium.

*Texture.*—Medium.

*Tendency to crack.*—None.

*Down.*—Short.

*Color.*—Yellow ground color (4-A-5) to (4-A-8). Overspread with red (10-B-7) to (10-B-8).

Flesh:

*Texture.*—Firm.

*Ripens.*—Even.

*Juice.*—Moderate.

*Flavor.*—Subacid to mild.

*Eating quality.*—Good.

*Color.*—Varies from light pale yellow (4-A-3) to rich golden yellow (4-A-7). Some fruit have red streaks near pit cavity. Pit cavity dull red (8-B-4).

Stone:

*Type.*—Freestone. Small flesh fragments adhere to some pit cavities on firm fruit.

*Size.*—Medium. Average length — 1 3/16". Average breadth — 1". Average thickness — $\frac{5}{8}''$.

*Base.*—Varies from rounded to straight.

*Apex.*—Acuminate.

*Surface.*—Irregularly furrowed toward apex, pitted toward base.

*Tendency to split.*—Very slight.

*Color.*—Reddish brown (9-C-6) to (9-C-7).

Use: Dessert.

Keeping quality: Good.

Shipping quality: Good.

The new variety of peach tree and its fruit herein described may vary in slight detail due to climatic, soil conditions and cultural practices under which the variety may be grown; the present description is that of the variety grown in the experimental orchard at Modesto, Calif.

We claim:

1. A new and distinct variety of peach tree as illustrated and described, characterized by its large size, vigorous, upright growth and bearing large, showy, double, pink flowers in the spring giving the effect of an ornamental flowering tree; the tree is further characterized by being a regular and productive bearer of large, firm, yellow flesh, freestone fruit with good eating quality and attractive red skin color.

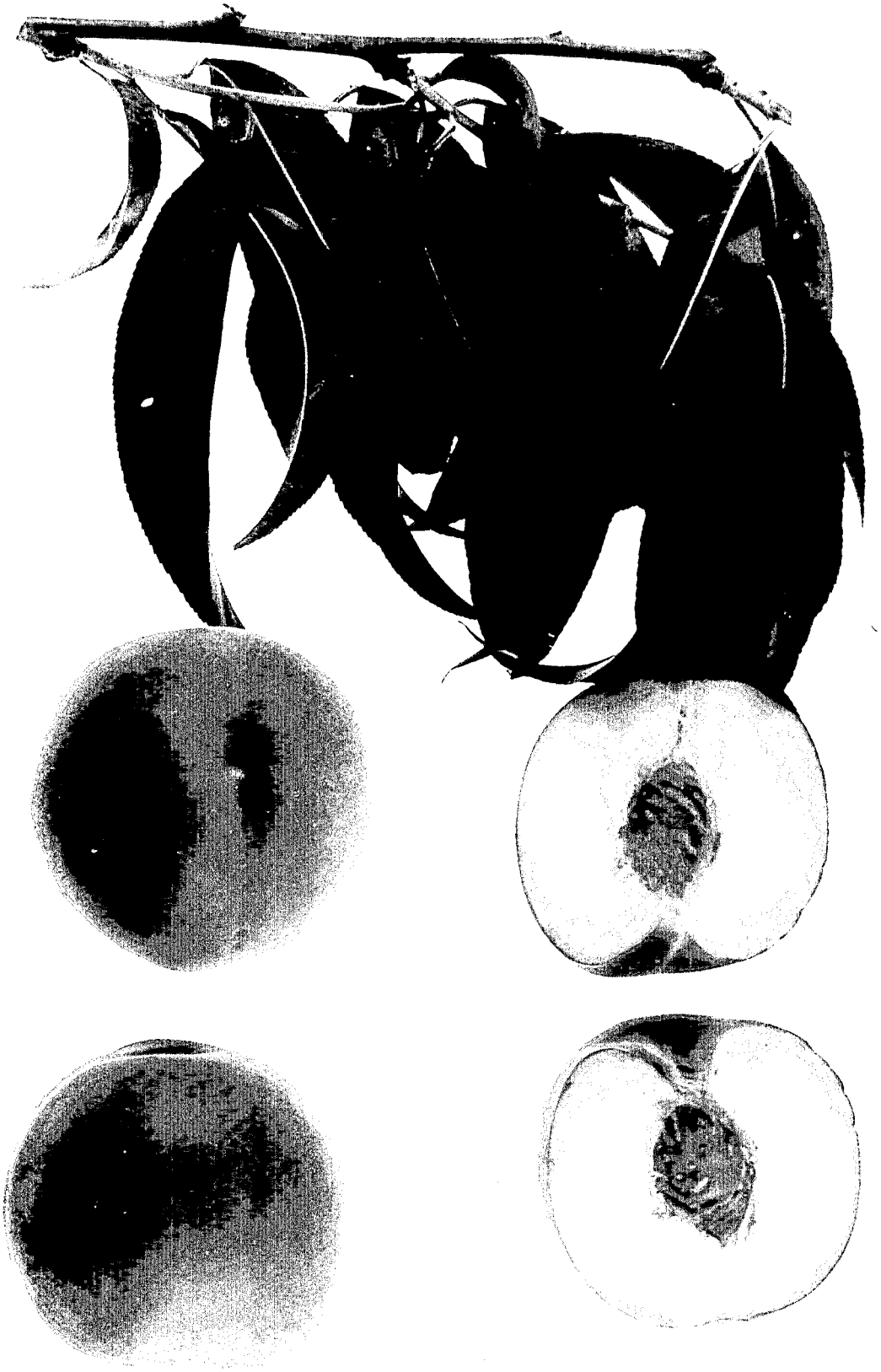

* * * * *